US008768455B2

(12) United States Patent
Teggatz et al.

(10) Patent No.: US 8,768,455 B2
(45) Date of Patent: Jul. 1, 2014

(54) TOPICAL APPLICATOR

(75) Inventors: Ross E. Teggatz, McKinney, TX (US); William Provence, Rio de Janeiro, TX (US)

(73) Assignee: Triune IP LLC, Richardson, TX (US)

( * ) Notice: Subject to any disclaimer, the term of this patent is extended or adjusted under 35 U.S.C. 154(b) by 0 days.

(21) Appl. No.: 13/495,219

(22) Filed: Jun. 13, 2012

(65) Prior Publication Data

US 2012/0316381 A1    Dec. 13, 2012

Related U.S. Application Data

(60) Provisional application No. 61/496,416, filed on Jun. 13, 2011.

(51) Int. Cl.
*A61N 1/08* (2006.01)
*A61N 2/00* (2006.01)
*A61N 7/00* (2006.01)
*A61F 7/00* (2006.01)

(52) U.S. Cl.
USPC .................................. 607/3; 600/9; 604/289

(58) Field of Classification Search
None
See application file for complete search history.

(56) References Cited

U.S. PATENT DOCUMENTS

| | | | | |
|---|---|---|---|---|
| 6,334,074 B1* | 12/2001 | Spertell | ......................... | 607/101 |
| 6,572,637 B1* | 6/2003 | Yamazaki et al. | .............. | 607/89 |
| 7,083,580 B2* | 8/2006 | Bernabei | ......................... | 601/15 |
| 7,141,049 B2* | 11/2006 | Stern et al. | ...................... | 606/41 |
| 7,473,251 B2* | 1/2009 | Knowlton et al. | .............. | 606/41 |
| 7,532,926 B2* | 5/2009 | Bernabei | ........................... | 607/3 |
| 2001/0003565 A1* | 6/2001 | McOsker et al. | ............. | 401/132 |
| 2004/0107974 A1* | 6/2004 | Paratore et al. | ................ | 132/218 |
| 2009/0093749 A1* | 4/2009 | Shalev et al. | ................... | 604/20 |
| 2010/0013610 A1* | 1/2010 | Schwieger | ................. | 340/407.1 |
| 2010/0274329 A1* | 10/2010 | Bradley et al. | .................. | 607/90 |

* cited by examiner

*Primary Examiner* — Brian T Gedeon
*Assistant Examiner* — Ankit Tejani
(74) *Attorney, Agent, or Firm* — Hovey Williams LLP

(57) ABSTRACT

Disclosed are advances in the arts with novel topical applicator apparatus for applying substances such as cleansers, cosmetic preparations and medications to the skin. The apparatus includes an applicator body having a power portion connected with an impulse portion, which in combination with an applicator head, transmits one or more various impulses to the skin supplemental to the substance applied. Exemplary preferred embodiments include configurations for providing mechanical and/or electrical or other impulses.

25 Claims, 4 Drawing Sheets

TOPICAL APPLICATOR

PRIORITY ENTITLEMENT

This application is entitled to priority based on Provisional Patent Application Ser. No. 61/496,416 filed on Jun. 13, 2011, which is incorporated herein for all purposes by this reference. This application and the Provisional Patent Application have at least one common inventor.

TECHNICAL FIELD

The invention relates to apparatus for the application of fluids for skin care and treatment. More particularly, the invention relates to apparatus for topical application of cleaners, conditioning agents, medications, and the like.

BACKGROUND OF THE INVENTION

In the field of skin care, many serums, moisturizers and specific conditioning formulations are available. Additionally, many medications are designed for topical application to the skin. It is known to apply a wide range of skin care and treatment products with either general purpose or application-specific applicator tools. Generally, available applicators only provide means for applying a liquid in contact with the skin, and/or some type of reservoir for supplying the portion of the applicator that makes contact with the skin. The inventors have observed that the applicators available in the art are not designed to promote reactions, e.g., electro-chemically, or thermo-chemically, etc., as a compliment to physically applying a liquid in contact with the skin. An additional problem with known skin applicators is that they do not provide feedback to the user as to the condition of the skin or the underlying tissue. Also, skin features such as blemishes, dark spots, and wrinkles are not detected, differentiated, or monitored to provide accurate diagnosis and tracking of a user's skin characteristics. Due to these and other problems and potential problems, novel and useful apparatus has been invented for the application of skin care products, including cleansing, cosmetic, and medical products, that include features for promoting interactions between the applied product and the skin, and which can be beneficial in improving skin and underlying tissue health.

SUMMARY OF THE INVENTION

In carrying out the principles of the present invention, in accordance with preferred embodiments, the invention provides advances in the arts with novel systems directed to useful and advantageous physically precise applicator apparatus, and applicator electronics for enhancing interactions between the skin and applied substances such as fluid(s). According to aspects of the invention, preferred embodiments include topical applicator apparatus endowed with electronic technology for enhanced sensing, monitoring, various forms of stimulation, and control.

According to one aspect of the invention, an example of a preferred embodiment of topical applicator apparatus includes an applicator body having an impulse portion suitable for driving by a power portion. An applicator head connected with the applicator body is designed for transmitting impulses received from the impulse portion to the skin of a user.

According to another aspect of the invention, in an exemplary embodiment the topical applicator apparatus is adapted to transmit a mechanical impulse.

According to another aspect of the invention, in an exemplary embodiment, topical applicator apparatus is adapted to transmit an electrical impulse.

According to another aspect of the invention, in an example of a preferred embodiment, topical applicator apparatus is adapted to transmit heating or cooling impulses.

According to another aspect of the invention, in an exemplary embodiment, topical applicator apparatus is configured for the transmittal of one or more fluids.

According to yet another aspect of the invention, an example of a preferred embodiment of topical applicator apparatus includes electronic sensor apparatus for sensing parameters present at the applicator head.

According to still another aspect of the invention, in an example of a preferred embodiment, topical applicator apparatus is equipped with position-determining technology.

According to additional aspects of the invention, in examples of preferred embodiments, topical applicator apparatus includes a control module for controlling impulse transmission, fluid dispensation and/or fluid mixing.

The invention has advantages including but not limited to providing one or more of the following features; precise applicator control, enhanced interaction between the skin of users and applied fluid, sensing and monitoring of skin characteristics and selected locations. These and other advantageous features and benefits of the present invention can be understood by one of ordinary skill in the arts upon careful consideration of the detailed description of representative embodiments of the invention in connection with the accompanying drawings.

BRIEF DESCRIPTION OF THE DRAWINGS

The present invention will be more clearly understood from consideration of the following detailed description and drawings in which.

References in the detailed description correspond to like references in the various drawings unless otherwise noted. Descriptive and directional terms used in the written description such as front, back, top, bottom, upper, side, et cetera; refer to the drawings themselves as laid out on the paper and not to physical limitations of the invention unless specifically noted. The drawings are not to scale, and some features of embodiments shown and discussed are simplified or amplified for illustrating principles and features, as well as advantages of the invention.

DESCRIPTION OF PREFERRED EMBODIMENTS

While the making and using of various exemplary embodiments of the invention are discussed herein, it should be appreciated that the present invention provides inventive concepts which can be embodied in a wide variety of specific contexts. It should be understood that the invention may be practiced with various skin preparations, primarily fluids, in some cases powders, and for various cosmetic and medical purposes without altering the principles of the invention. For purposes of clarity, detailed descriptions of functions, components, and systems familiar to those skilled in the applicable arts are not included. In general, the invention provides novel and advantageous advances in terms of improving applicators with the application of principles relating to mechanical, fluid-flow, thermal, electrical, optical and other measurements and manipulations.

Figure 1:
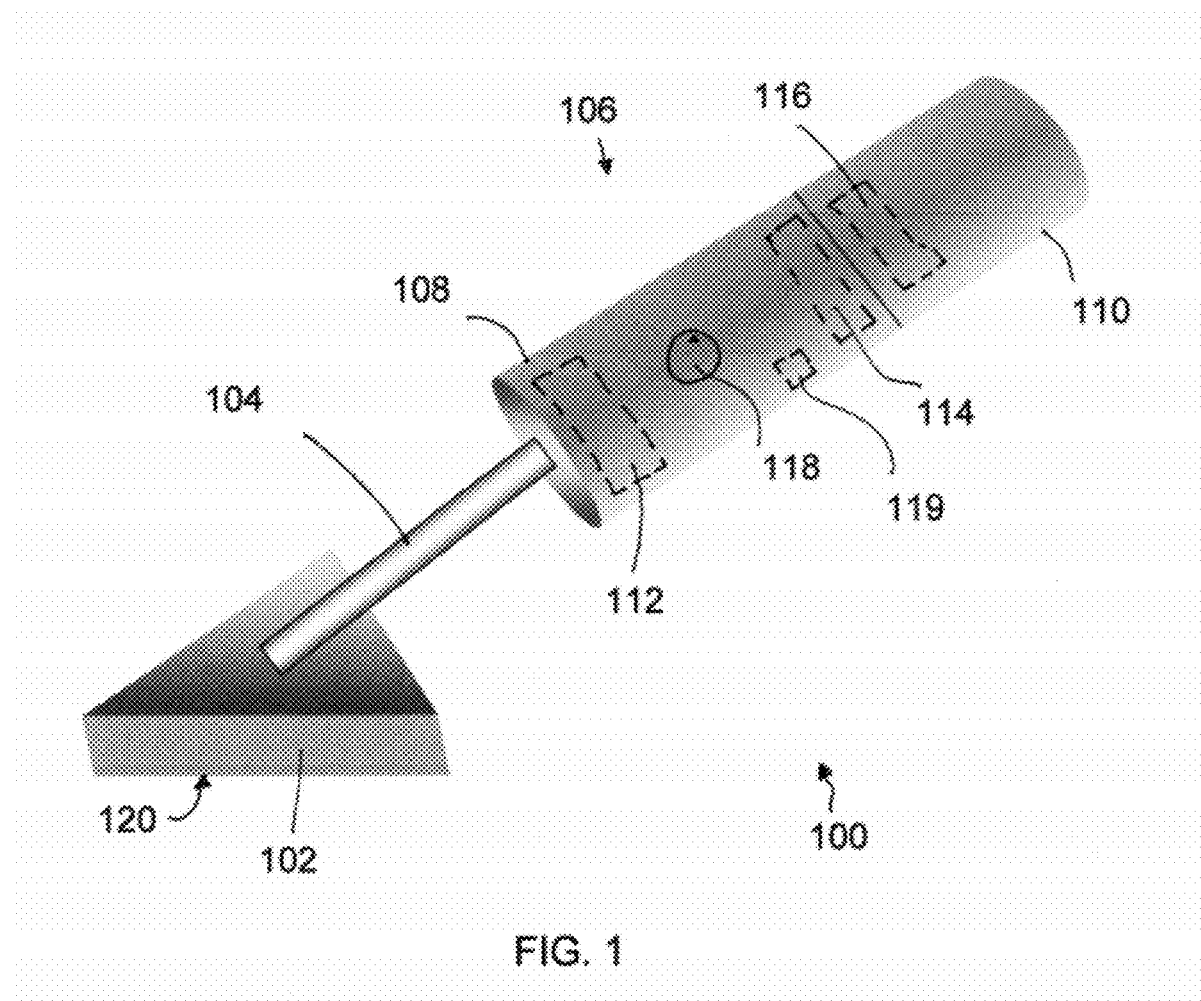
FIG. 1 is a perspective view of a topical applicator in an example of preferred embodiments of the invention.

Referring initially to FIG. 1, an example of a preferred embodiment of topical applicator apparatus 100 is shown. An applicator head 102 is connected by a wand 104 to an applicator body 106. The body 106 has an impulse portion 108 and a power portion 110. In some embodiments, the body may also include a reservoir 112 in fluid communication with the applicator head 102. In operation, the impulse portion 108 is adapted to transmit impulses, in this example mechanical motion, to the applicator head 102 through the wand 104. The mechanical movement generated by the impulse portion 108 is facilitated by a vibrating element such as an electric motor 114 within, which is powered by an energy storage element 116 such as a battery, battery bank, or capacitor(s) provided within the power portion 110. Preferably, a suitable charging port is provided for replenishing power. The motion of the applicator head 102 may preferably be adjusted manually using a manual control 118 situated on the impulse portion 108, or adaptive control circuitry in a control module 119 may be used to provide a selected frequency of movement, such as a resonant frequency, for example. Under these conditions, skin stimulation and toning of underlying muscle tissue can be achieved. The frequency may also be modulated over a selected range to provide a pulsating impulse, which may provide additional massaging benefits. It is believed that through the use of this apparatus, and variations thereof employing the same operating principles, the underlying skeletal muscle may achieve improved tone as well as increased relaxation. In turn, the improved tone of the underlying skeletal muscle is believed to have a healthy effect on the skin, having a tendency to mitigate the tendency of aging facial muscles to sag, for example. It is believed that in some cases the effect results in a decrease of "worry lines" in the face. In embodiments equipped with a reservoir, e.g., 112, a fluid such as skin conditioner or medication may be dispensed through the applicator head 102. In embodiments lacking the optional reservoir, the applicator may be dipped and/or coated with fluid, or in some cases powder, for application to the skin. In either scenario, the mechanical impulses applied to the skin by the apparatus 100 are provided for stimulating the skin and/or agitating the fluid (or powder) being applied in order to enhance chemical reaction(s) and/or contact with the skin. As further addressed below, in a configuration with an appearance substantially similar to that depicted in FIG. 1, the electric motor 114, and its mechanical movement, may be supplemented by electrical and/or thermal impulses transmitted to electrodes in the applicator head 102 provided for that purpose. Optionally, the motor 114 may be omitted if mechanical impulses are not desired.

Figure 2:
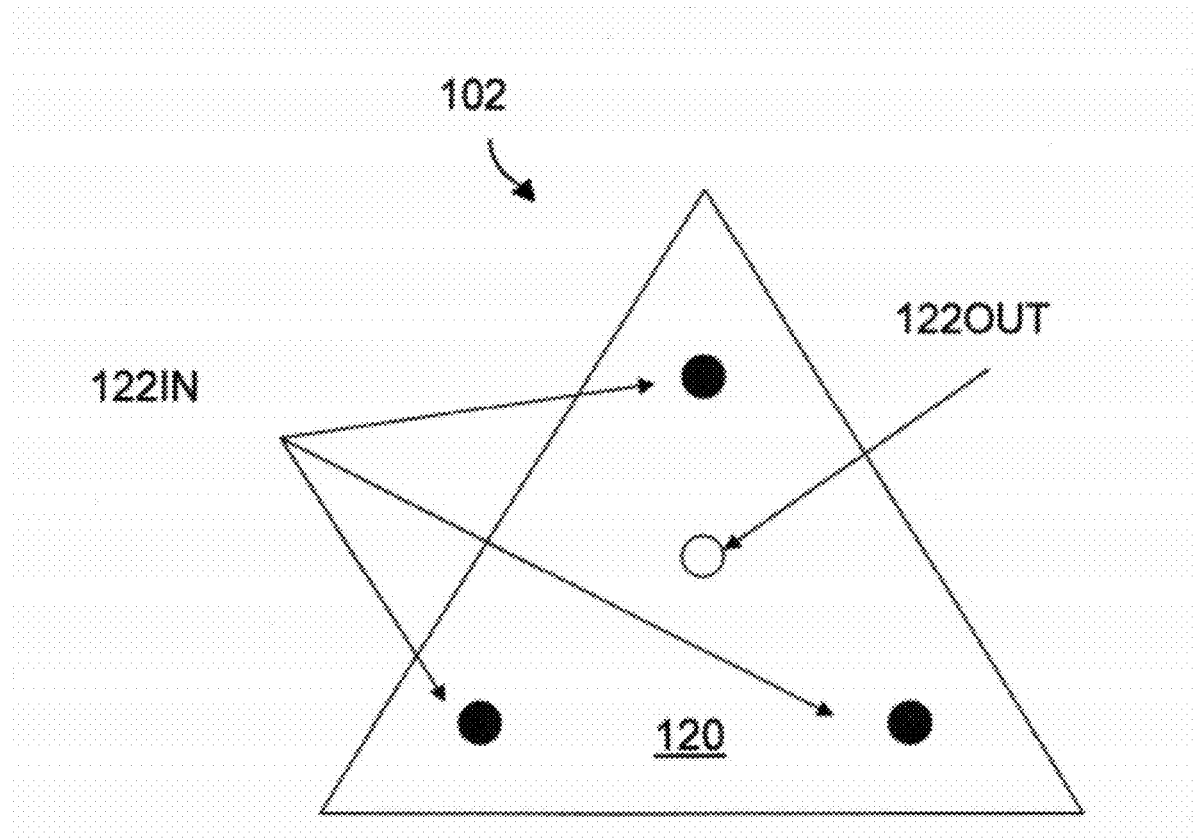
FIG. 2 is a partial view of a topical applicator in an example of preferred embodiments of the invention.

Now referring primarily to FIG. 2, a partial view of a preferred embodiment of an applicator head 102 shows an example of the applicator surface 120. A plurality of apertures 122 are provided. The apertures 122 are preferably interconnected within the applicator head 102 in order to direct fluid flow. As shown, one or more output apertures $122_{OUT}$ may be accompanied by one or more intake apertures $122_{IN}$. FIG. 2 shows an implementation in which intake apertures $122_{IN}$ flank a central output aperture $122_{OUT}$. Flow directions may be reversed from this arrangement and may also be implemented without departure from the invention in other combinations to provide a flowing and/or scrubbing action at the applicator surface 120. It should be appreciated that interchangeable, removable, applicators 102 having various surfaces 120 and aperture 122 patterns may be used with a suitable body unit 106 (FIG. 1).

Figure 3A:
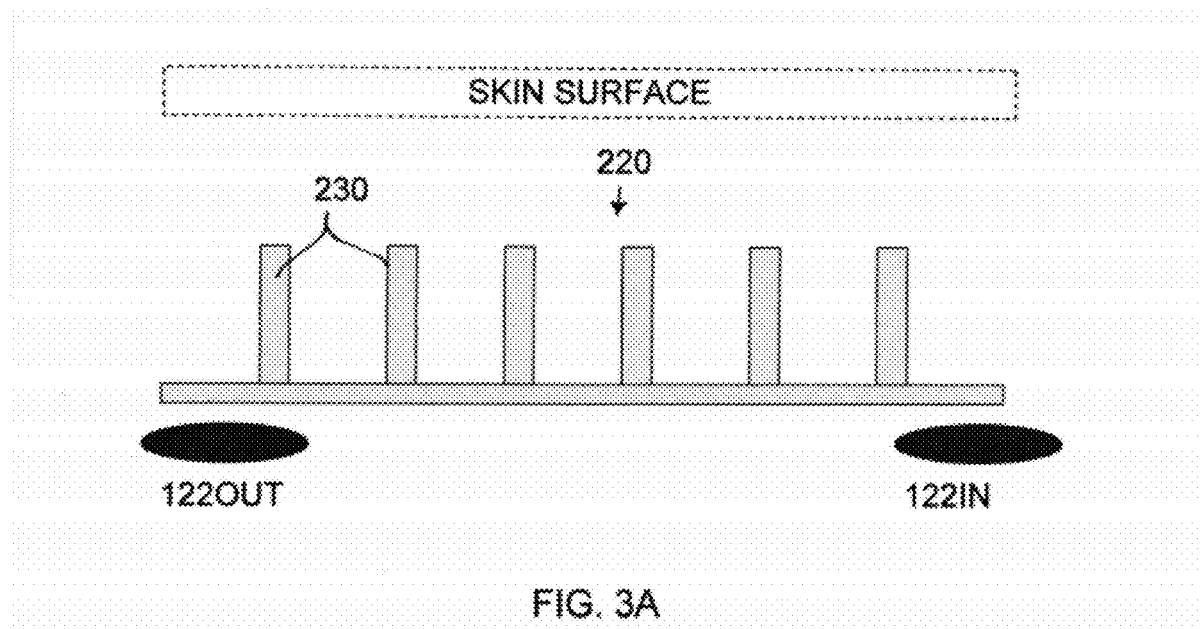
FIGS. 3A and 3B are partial side views showing the operation of a topical applicator in an example of preferred embodiments of the invention.
Figure 3B:
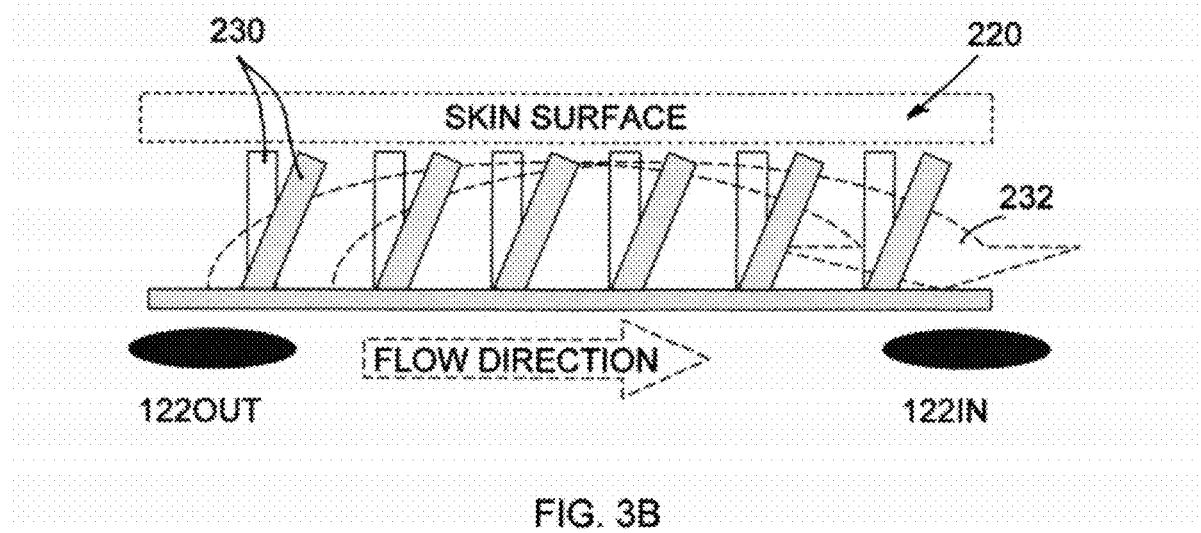

FIGS. 3A and 3B depict partial cutaway side views of another embodiment of an applicator head 202. As shown in this exemplary embodiment, the surface 220 of the applicator head 202 may be provided with micro-fibers 230 to facilitate and enhance the introduction or removal of material to/from the skin. The micro-fibers 230 are preferably configured to provide micro-scrubbing of the skin aided by the fluid flow illustrated by arrow 232 in FIG. 3B. This may be performed in one direction of flow, or flow may be periodically reversed, e.g., re-directed from in-to-out and out-to-in, producing a micro-brushing effect at the surface 220 applicator head 202, and thus at the surface of any adjacent skin. Alternatively, differences in electrical potential, magnetic field, and/or temperature gradient can also be used to manage the micro-movement of the micro-fibers 230 on the applicator head surface 220 in a similar manner as further described herein.

Figure 4:
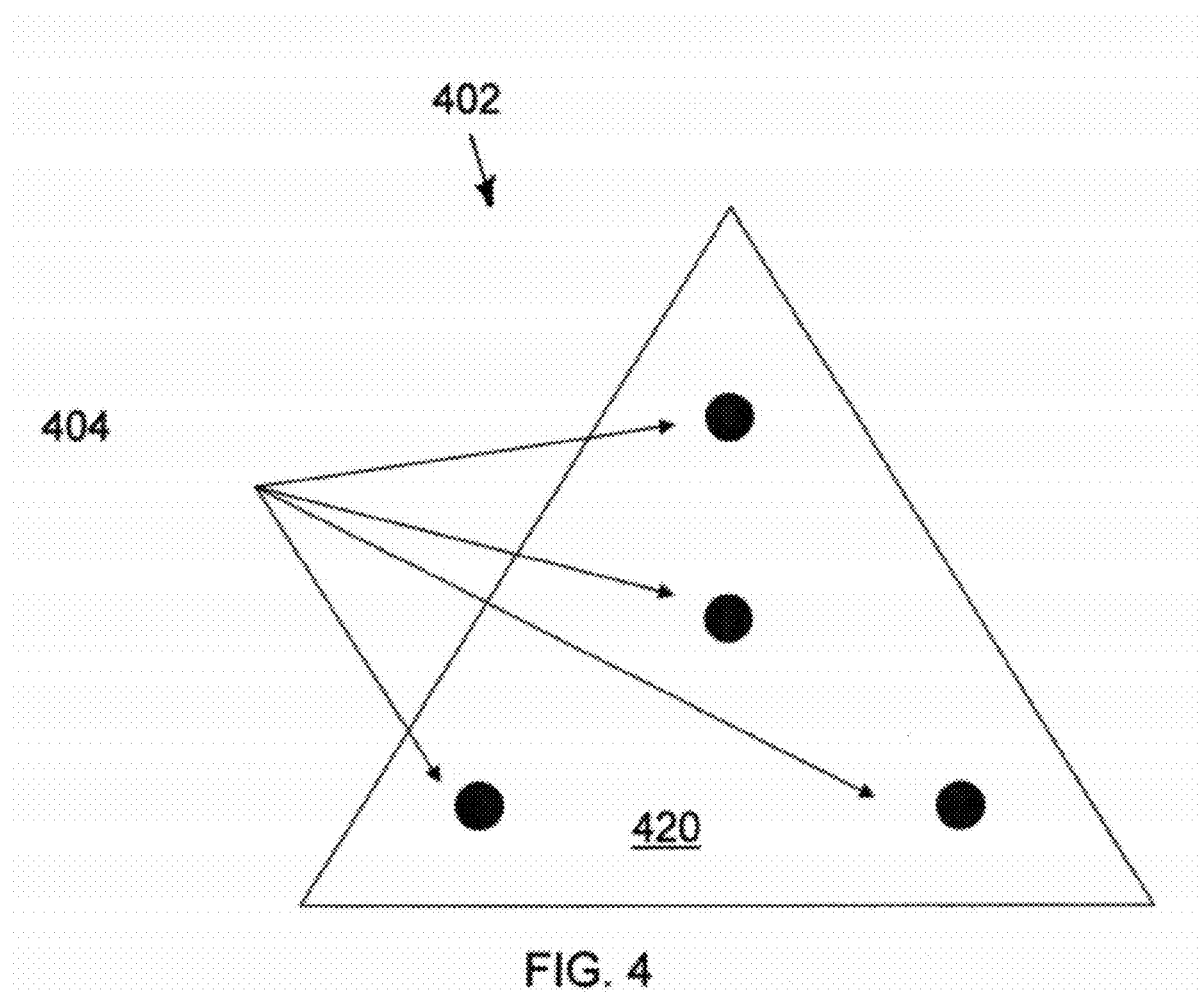
FIG. 4 is a partial view of a topical applicator in an example of preferred embodiments of the invention.

An alternative embodiment of an applicator head 402 is depicted in FIG. 4. Electrodes 404 are shown on the surface 420 of the applicator head 402. The electrodes 404, e.g., electronic probes or sensors, preferably perform the function of taking electrical measurements indicative of conditions on the applicator head and/or adjacent skin. Measurements of changes in electrical characteristics at the skin can provide feedback relating to skin health, for example, by comparison of measurements over a period of time in a certain location. This information can also provide locations of electrical deviations on the skin surface indicative of skin condition relating to healthy areas and/or the existence of potential ailments. Similarly, electro-stimulation by transmitting electrical impulses through the electrodes 404 can be used to stimulate circulation in the skin and the skeletal muscle substructures underneath. In addition, electrical impulses can provide a charge at the skin surface, which can assist in electro-chemical reactions between an applied fluid and the skin. The electrodes 404 of the applicator along with a suitable fluid formulation can also be used to maintain a conductive interface with the skin surface. This can enhance the electro-chemical reaction by providing an equipotential charge across the skin and/or applicator surface 420. This may be used to assist in the promotion of improved muscle tone as well as enhanced blood flow to the skin sub-structure. In embodiments having an applicator with microfibers 330 (FIGS. 3A-3B), the micro-fibers in the material can be made such that they are directionally charged. In this way, by the transmission of electrical impulses a charge potential can be placed across the micro-fibers 330 causing them to bend in accordance with the electrical potential gradient applied. In this way, the orientation of the microfibers 330 may be controlled toward or away from particular areas of the skin. The movement of the microfibers 330 may also be used to impart a scrubbing action to the applicator head 102. It is contemplated that the electrodes of the apparatus may be used in the context of imparting a charge to a skin preparation prior to application to the skin of a user. That is, the electrodes of the applicator may be used to stimulate electrons in a skin preparation liquid, cream or gel, and the charged preparation may then be applied to the skin using the applicator, another tool, or even a user's hand, providing advantages inherent in using the apparatus for pre-charging the preparation.

Many variations of the topical applicator apparatus shown and described are possible within the scope of the invention. Implementations may include heat sensors and/or heating elements positioned in the applicator head 102 in an arrangement similar to that shown in FIG. 4. Thermal measurements may be made using an applicator head so equipped, or heating, or cooling impulses may be applied using such apparatus. Selective heating and/or cooling can be used to provide a constant or a gradient of heating and/or cooling. This can help promote thermal-chemical reactions with the skin or in a liquid formulation applied on the skin, or a combination thereof. Use of an accurate x-y-z positioning device, such as but not limited to, a GPS locator and/or a low-G accelerometer can provide three-dimensional positioning to provide delta-thermal responses. These delta-thermal responses can lead to identification of potential underlying thermal-chemical or thermal-organic deviations, which can pinpoint potential thermal hot-spots on the skin surface where ailments or skin conditions may exist, such as sites of inflammation that could activate the application of specific skin care solutions with anti-inflammatory effects, or, in the case of acne for example, anti-bacterial effects. In applicator heads also equipped with micro-fibers, the micro-fibers in the material can also be made so they have a thermal-mechanical reactive nature so as to bend in a predetermined direction depending on the thermal gradient applied. This can provide a scrubbing action to the applicator head. In conjunction with an embedded GPS locator or low-G accelerometer, the directionality of the scrubbing, heating/cooling actions can be correlated with pre-determined maps of the facial features of a user, including orientation of muscle fibers and/or sites of particular interest.

In another potential variation of the apparatus of the invention, an optical or thermal-optical imaging device can also be used in conjunction with an accurate x-y-z positioning device to provide feedback on how topical fluid is applied to a particular site. This information may be used for example with adaptive control devices to further dispense topical fluid from a reservoir in the applicator body. The dosage may be adjusted manually as well. The optical monitoring devices can also provide diagnostics such as pinpointing skin blemishes or other ailments and conditions. Additional fluids or differently formulated fluids can be responsively applied in specific areas to provide pinpoint treatment. It is contemplated that the composition of a topical fluid can be adjusted based on feedback from the various sensors embedded in the applicator head in order to provide formulations tailored for a particular application. Conductive or specific conductivity elements can be used to provide flow of the formulation or switching of the formulation applied. Thermal or specific thermal elements can be used to provide flow of the formulation or choice of formulation applied. Thermal-chemical effects or electrical-chemical effects of the fluid can also be used to realize advantages by inducing a reaction in the fluid directly at the skin surface when applied. Thus, the apparatus can be used to provide levels of mendicants that can be directly dispensed at the skin, skin sub-surface, and circulatory system. The basis of localized position information can optionally be provided by a benchmark device that is consistently localized to the same region of the face during each use of the instrument such as eyeglasses, a mouth-piece or nasal clip. The benchmark device provides orientation coordinates through wired or wireless communication with the control portion of the applicator apparatus.

The apparatus of the invention provide one or more advantages including but not limited to, precise applicator control, enhanced interaction between the skin of users and applied fluid, sensing and monitoring of skin characteristics and selected locations, efficiency, safety, convenience, and reduced cost. While the invention has been described with reference to certain illustrative embodiments, those described herein are not intended to be construed in a limiting sense. For example, variations or combinations of steps or materials in the embodiments shown and described may be used in particular cases without departure from the invention. All of the aspects of implementations of control, sensing, and dispensation of fluids can be combined in various ways. For example, the principles and apparatus of the invention may be adapted to use electrodes as shown to impart an electrical charge to a liquid prior to topical application. This may be accomplished independently from a particular applicator for making contact with the skin. Various modifications and combinations of the illustrative embodiments as well as other advantages and embodiments of the invention will be apparent to persons skilled in the arts upon reference to the drawings, description, and claims.

We claim:

1. Topical applicator apparatus comprising:
   an applicator body, the applicator body comprising a power portion operably coupled to an impulse portion;
   an applicator head connected with the applicator body; and
   a positioning apparatus;
   wherein the applicator head is configured for receiving an impulse from the impulse portion and for transmitting the impulse topically to the skin of a user, wherein the applicator head comprises a plurality of apertures configured to come in contact with the skin of a user, wherein the positioning apparatus comprises an x-y-z positioning device.

2. The topical applicator apparatus according to claim 1 wherein the impulse portion is adapted to transmit a mechanical impulse.

3. The topical applicator apparatus according to claim 1 wherein the impulse portion is adapted to transmit an electrical impulse.

4. The topical applicator apparatus according to claim 1 wherein the impulse portion is adapted to transmit a thermal impulse.

5. The topical applicator apparatus according to claim 1 wherein the impulse portion is adapted to transmit a fluid.

6. The topical applicator apparatus according to claim 1 wherein the impulse portion is adapted to transmit a magnetic field.

7. The topical applicator apparatus according to claim 1 further comprising a sensor apparatus configured to measure changes in the skin of a user.

8. The topical applicator apparatus according to claim 1 wherein the applicator head further comprises a sensor apparatus configured to measure changes in the skin of a user.

9. The topical applicator apparatus according to claim 1 wherein the applicator head comprises the positioning apparatus.

10. The topical applicator apparatus according to claim 1 further comprising one or more fluid reservoirs.

11. The topical applicator apparatus according to claim 1 wherein the applicator head further comprises a surface having micro-fibers.

12. The topical applicator apparatus according to claim 1 wherein the applicator head further comprises a surface having one or more electrodes.

13. The topical applicator apparatus according to claim 1 further comprising a control module configured for controlling transmitted impulses.

14. The topical applicator apparatus according to claim 1 further comprising a control module configured for receiving sensor signals.

15. The topical applicator apparatus according to claim 1 further comprising a control module configured for controlling fluid dispensation.

16. The topical applicator apparatus according to claim 1 further comprising a control module configured for controlling fluid mixing.

17. Topical applicator apparatus comprising:
- an applicator body, the applicator body comprising a power portion operably coupled to an impulse portion;
- an applicator head connected with the applicator body; and
- a positioning apparatus;
- wherein the applicator head is configured for receiving an electrical impulse from the impulse portion and for transmitting the electrical impulse topically to the skin of a user, wherein the applicator head comprises a plurality of apertures configured to come in contact with the skin of a user, wherein the positioning apparatus comprises an x-y-z positioning device.

18. Topical applicator apparatus comprising:
- an applicator body, the applicator body comprising a power portion operably coupled to an impulse portion;
- an applicator head connected with the applicator body; and
- a positioning apparatus;
- wherein the applicator head is configured for receiving a mechanical impulse from the impulse portion and for transmitting the mechanical impulse topically to the skin of a user, wherein the applicator head comprises a plurality of apertures configured to come in contact with the skin of a user, wherein the positioning apparatus comprises an x-y-z positioning device.

19. The topical applicator apparatus according to claim 1 wherein the applicator head is configured to transmit one or more fluids onto the skin of a user.

20. The topical applicator apparatus according to claim 19 wherein the applicator head comprises one or more electrodes.

21. The topical applicator apparatus according to claim 1 wherein the applicator head comprises a heat sensor and/or a heating element.

22. The topical applicator apparatus according to claim 1 wherein the x-y-z positioning device comprises a GPS locator or a low-G accelerometer.

23. The topical applicator apparatus according to claim 11 wherein the micro-fibers are directionally charged.

24. The topical applicator apparatus according to claim 17 wherein the x-y-z positioning device comprises a GPS locator or a low-G accelerometer.

25. The topical applicator apparatus according to claim 18 wherein the x-y-z positioning device comprises a GPS locator or a low-G accelerometer.

* * * * *